United States Patent [19]
DeTore et al.

[11] Patent Number: 5,732,397
[45] Date of Patent: Mar. 24, 1998

[54] AUTOMATED DECISION-MAKING ARRANGEMENT

[75] Inventors: Arthur W. DeTore; Russell D. Suever, both of Fort Wayne, Ind.

[73] Assignee: Lincoln National Risk Management, Inc., Fort Wayne, Ind.

[21] Appl. No.: 851,811

[22] Filed: Mar. 16, 1992

[51] Int. Cl.$^6$ .................................................. G06F 17/60
[52] U.S. Cl. .................... 705/1; 705/2; 705/35; 395/51
[58] Field of Search .................... 364/400, 148, 364/401, 408; 395/10, 51, 61, 600, 650

[56] References Cited

U.S. PATENT DOCUMENTS

| | | | |
|---|---|---|---|
| 4,346,442 | 8/1982 | Musmanno | 364/408 |
| 4,376,978 | 3/1983 | Musmanno | 364/408 |
| 4,591,983 | 5/1986 | Bennett et al. | 364/403 |
| 4,595,982 | 6/1986 | Burt. | |
| 4,597,046 | 6/1986 | Musmanno et al. | 364/408 |
| 4,622,013 | 11/1986 | Cerchio | 434/118 |
| 4,642,768 | 2/1987 | Roberts | 364/408 |
| 4,648,044 | 3/1987 | Hardy et al. | 364/513 |
| 4,658,370 | 4/1987 | Erman et al. | 364/513 |
| 4,674,044 | 6/1987 | Kalmus et al. | 364/408 |
| 4,722,055 | 1/1988 | Roberts | 364/408 |
| 4,741,043 | 4/1988 | Bacus | 364/413.13 |
| 4,754,410 | 6/1988 | Leech et al. | 364/513 |
| 4,766,539 | 8/1988 | Fox | 364/401 |
| 4,829,426 | 5/1989 | Burt | 364/300 |
| 4,831,526 | 5/1989 | Luchs et al. | 364/401 |
| 4,884,218 | 11/1989 | Agnew et al. | 364/513 |
| 4,975,840 | 12/1990 | DeTore et al. | 364/401 |
| 5,005,143 | 4/1991 | Altschuler et al. | 364/554 |
| 5,065,338 | 11/1991 | Phillips et al. | 395/51 |
| 5,131,074 | 7/1992 | Nakamura et al. | 395/61 |
| 5,278,751 | 1/1994 | Adiano et al. | 364/402 |

OTHER PUBLICATIONS

"Using Experience in Learning and Problem Solving", by P. Koton ©Oct. 1988 pp. 1–97.
"Using a Case Memory to Integrate Case Based and Casual Reasoning" by Phyllis Koton, Aug. 23, 1988 pp. 74–81.
Everest: Database Management. 1986 McGraw–Hill Inc. p. 746.

*Primary Examiner*—Robert A. Weinhardt
*Attorney, Agent, or Firm*—Barnes & Thornburg

[57] ABSTRACT

An automated system for use in decision-making, comprises input, output processing and storage capabilities. The storage and processing portions of the system include a number of components which receive information and data specific to a selected topic of decision-making. The components perform data collection, screening and decision-making functions. The system compares received data to previously stored data and identifies received data which does and does not correspond to the previously stored data. If the data does correspond, the system implements a first decision operation. If the received data does not correspond, the system determines the nature and degree of such non-correspondence, and implements a decision operation which is reflective of the nature and degree of the non-correspondence. If the nature and degree of non-correspondence cannot be determined, additional data pertaining to the selected topic is requested and compared to the previously stored data in an iterative manner. Discrepancies existing between corresponding elements of data are identified. The system also identifies a plurality of alternative options for the first and second decision operations, each of which may alternatively be selected to form at least a part of the decision operation. Data relating to the decision operations implemented are stored and compared to subsequently received data relating to outcomes. The system may be modified based on this comparison.

37 Claims, 4 Drawing Sheets

AUTOMATED DECISION-MAKING ARRANGEMENT

BACKGROUND AND SUMMARY OF THE INVENTION

This invention relates generally to decision-making and, more particularly, to a method and apparatus for use in automated decision-making processes.

Rational decision-making processes can be viewed as including the steps of problem definition, criteria identification, criteria weighting and alternative choice generation. Each alternative choice is rated on the basis of the criteria, and an optimal alternative is chosen for implementation. In most processes, these steps take place iteratively over time.

In decision-making processes, specific information on the subject matter of the decision to be made is correlated against background knowledge. Background declarative knowledge for decision-making on any topic can be viewed as a model which comprises many elements, including a description of the topic, its components and how they function, the relationships among various components, characteristics of the various components, the purpose of the decision-making, and the criteria and weights which are to be applied.

Decision-making is difficult because it generally requires simultaneous consideration of many specific and general factors. Managing this process within a "manual" or "non-automated" environment is difficult since much of the decision-making process is completed by the mental processes of individual decision-makers. Generally, the only documentation which may be concurrently or subsequently available to manage or evaluate the decision is that which the decision maker is capable of or decides to reveal. Hence, it may be difficult to determine the extent or accuracy of the background knowledge applied in the decision-making process, the amount or source of information about the subject decision which was used in the decision-making process, or the correctness or consistency with which the background knowledge or other information was applied or considered. Accordingly, the overall quality of the final decision may be difficult to assess.

An object of the present invention is to provide an automated system for use in decision-making processes which will improve the quality and consistency of decisions made.

Another object of the present invention is to provide an automated system for use in decision-making processes which will facilitate the management and evaluation of decision-making.

These and other objects are achieved in an automated system for use in decision-making processes which comprises input means, output means, information processing means and storage means. The storage and processing means comprises a plurality of "components." Each component is adapted to receive information and data specific to a selected topic of decision-making. The plurality of components include data collection means for eliciting and receiving data pertaining to the selected topic of decision-making, screening means for comparing data received by the data collection component to data previously stored in the storage means and for implementing a first decision operation if the received data corresponds to the previously stored data, and decision-making means for identifying received data which does not correspond to the previously stored data. The system further includes means for determining the nature and degree of any such non-correspondence, and means for implementing a second decision operation which is reflective of the nature and degree of the non-correspondence existing between the received data and the previously stored data. The nature of the non-correspondence is preferably determined by reviewing the non-corresponding received data and comparing that data to previously stored data to determine the nature of the non-correspondence. The non-corresponding data may be compared to data representative of at least one of a plurality of previously stored model data sets to determine the nature of non-correspondence existing between the received and previously stored data. The degree of non-correspondence may also be determined by reviewing the non-corresponding received data and comparing that data to previously stored data. The non-corresponding data may be compared to a previously stored range of data values to determine the degree of non-correspondence existing between the received and previously stored data.

One embodiment of the present invention includes means for identifying received data which does not correspond to previously stored data and for which the nature and degree of non-correspondence cannot be determined. This embodiment further includes means for requesting additional data pertaining to the selected topic of decision-making process, means for comparing the additional data to previously stored data, and means for implementing one of the first and second decision operations. The additional data is further compared to the previously received data, and any discrepancies existing between corresponding elements of data are identified.

The means for implementing one of the first and second decision operations comprises means for identifying a plurality of alternative options, each of which may be alternatively selected to form at least a part of the decision operation, means for comparing expected outcomes of the options, and means for selecting from among the options. This or other embodiments of the invention further comprise means for storing data relating to the decision operations implemented, means for comparing the data to subsequently received data relating to an outcome of the decision-making process, and means for adding, deleting or modifying the information, data or instructions in at least one of the components based on this comparison.

Other objects, advantages and novel features of the present invention will become apparent from the following detailed description of the invention when considered in conjunction with the accompanying drawings.

DETAILED DESCRIPTION OF THE DRAWINGS

Figure 1:
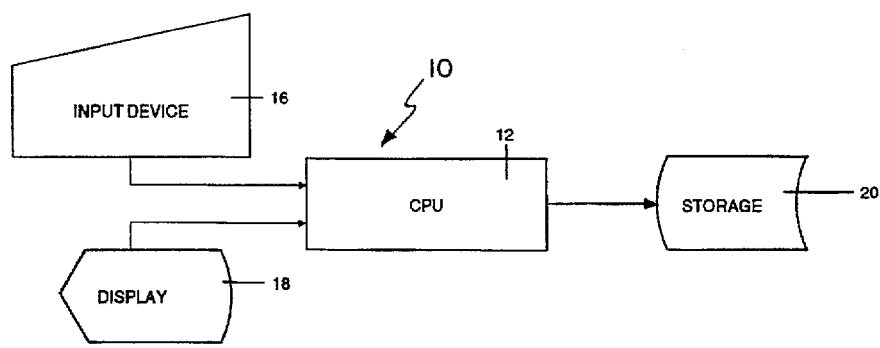
FIG. 1 shows a block diagram of a generalized computer system suitable for use in practicing the present invention.

FIG. 1 shows a generalized computer system 10 suitable for use in practicing the present invention. System 10 includes a central processing unit (CPU) 12, an input device 16, such as a keyboard, and a display 18, such as a standard cathode ray tube monitor. System 10 further includes a storage element represented by block 20, which is illustrated in greater detail in FIG. 2.

Although the computer system of FIG. 1 represents "conventional" computer technology (which may be well-suited to the practice of the present invention), it should be clearly understood that the practice of the present invention is not limited to such technology. Computational systems based upon biocomputing techniques (such as neural nets, L-Systems, fractals and iterated function systems, genetic algorithms and fuzzy logic), as well as other computational technologies may also be used.

Figure 2:
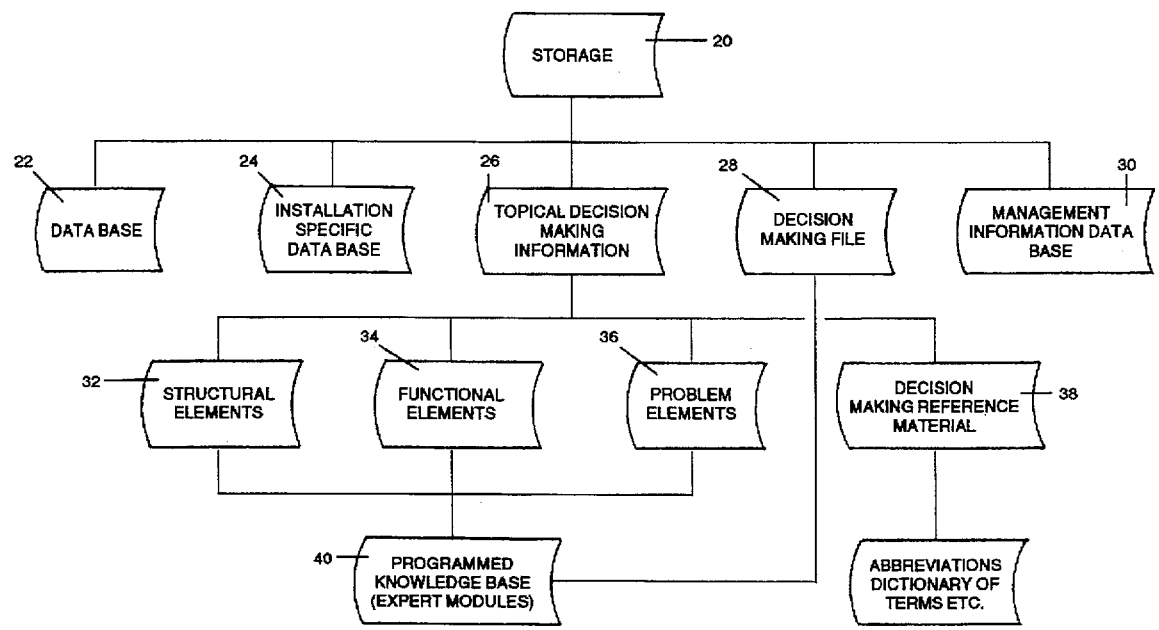
FIG. 2 shows a block diagram which illustrates the logical organization of the storage device of FIG. 1.

FIG. 2 shows a block diagram which illustrates a preferred logical organization of storage element 20. Briefly, storage element 20 comprises a data base 22, an installation specific data base 24, topical decision-making information (block 26), a decision-making file 28 and a management information data base 30. Data base 22 may contain general information which is relevant to the subject matter at hand. For instance, if the decision-making process relates to an investment decision, data base 22 may contain stock indices, prevailing interest rates, historical and trend financial data, and related information.

Installation specific data base 24 contains rules, guidelines, procedures and other information specific to a particular user. In the financial example referred to above, installation specific variables within data base 24 may include, but are not limited to, required rates of return, risk tolerance indicators, the identification of particular groupings of stocks or other investment instruments, and preferred economic indicators. The information in data base 24 may be modified from time to time to reflect changing investment strategies and preferences or general economic conditions.

Topical decision-making information (block 26) includes the information base which drives the decision-making system. This information embodies the general model or theory which is used to solve problems and reach a decision. Information base 26 may be visualized as comprising a number of elements, including structural elements, functional elements, problem elements and decision-making reference material. These elements and materials are graphically illustrated by blocks 32, 34, 36 and 38, respectively. Structural elements 32 include the major components of declaratory knowledge used in the subject decision process. In the case of the investment example previously referred to, the "elements" in block 32 may be specific financial instruments (e.g., stocks, bonds, certificates of deposit, etc.). If the topic of decision-making relates to medical diagnosis, the "elements" in block 32 may include anatomical features of the human body.

Functional elements 34 comprise elements of information which relate to how the structural elements in block 32 work or function. For the investment example referred to above, such information may relate to how money is made from stocks, bonds and other investment instruments. In the medical example, such elements may include information relating to how the anatomical elements of block 32 function, or the role each element plays in larger anatomical systems.

The problem elements of block 36 include statements or definitions of problems which may occur or be encountered with the structural elements of block 32, or their functional characteristics as defined in block 34. In the investment example, such problems may include decreases in the value of stocks or bonds, defaults on loans or other obligations, or problems resulting from adverse weather conditions, wars or other natural and man-made disasters. In the medical example, problem elements may include statements and definitions relating to diseases or disorders of anatomical elements or systems. Programmed knowledge bases, which may include expert modules or systems (block 40), may be employed by the system to isolate and identify problems which may be encountered in the course of decision-making activity, as is more fully explained below.

Decision-making reference material 38 includes a "library" of abbreviations, a dictionary of terms, and other reference materials which are to be utilized in the decision-making process. The material which is represented by block 38 may be stored in a manner which facilitates usage by the system in the automated decision-making process, and in a form which may be readily available to a human decision-maker when appropriate or desired.

Each of the elements illustrated by blocks 32, 34 and 36 may include a programmed knowledge base having one or more expert modules which are utilized in the automated decision process. These modules are graphically and collectively represented by block 40. Expert modules in knowledge base 40 may include modules which isolate specific structural elements of interest in a particular decision-making situation, modules which define how specified components function and how the functioning of components in a particular situation may relate to "normal" or expected functionality, modules which define and/or identify problems which may exist with particular structural elements or functions, and modules which define structural and functional abnormalities.

Decision-making file 28 contains criteria, alternatives, weighting functions, utilities and other information useful in making decisions and selecting alternative decision paths. For example, in different situations different strategies can be used in decision making. For a problem or non-correspondence with a limited number of options and a one-to-one correspondence between the presentation of the problem or non-correspondence and the possible solution, a deterministic or simple rule-based approach can be taken. In the case of a person complaining of a sore throat and having redness in the back of the throat, the diagnosis of pharyngitis or a throat infection is very straight-forward and can be made with a deterministic approach. In other situations, however, a probabilistic approach may be necessary. In interpreting a very complex test, such as an exercise stress test, although a deterministic strategy could be used to equate a positive test with having heart disease, a decision should be made with a probabilistic strategy weighing the false positive rate and the false negative rate to determine the likelihood that someone with a positive test does indeed have heart disease.

In cases where statistics to determine false positive or false negative rates are not available and a probabilistic approach cannot be used, a model-based or causal strategy may be needed for problem solving. In this instance, because there is not a simple one-to-one correspondence, the decision-making process requires a model for comparison with the present problem or non-correspondence to determine the possible solution. For example, a decision process may involve diagnosing a patient having swollen legs and shortness of breath. Although this may represent two separate problems, a causal or model-based strategy could note that the person has heart trouble because the heart is a pump and if it is not pumping well fluid backs up on its right side causing swelling of the legs and on its left side causing fluid in the lungs which causes shortness of breath. In this way, a model has been superimposed on the anatomy and physiology of the heart and used to make the decision about the nature of the problem. Similarly, making the same decision using the criteria of quality of life versus length of survival or cost may modify a decision. Decision file 28 allows these different strategies, criteria and other information to be stored. As indicated in FIG. 2, decision-making file 28 may also contain programmed knowledge, including expert systems, which are useful, for example, in defining and selecting alternatives in a particular decision-making process.

Management information data base 30 contains the results of individual decisions made by the system and each decision maker utilizing the process. Data base 30 may be reviewed by a decision manager, along with selected information from the other data bases, to improve the decision-making capabilities of the system. The information which may be useful in this review includes the information available to the decision maker, the alternative decision paths considered and criteria applied in the decision-making process, the various levels of expertise of different decision makers, and other variables affecting the decision-making process. From the information stored in the management information data base, the quality and consistency of decisions made using the apparatus and method of the present invention-can be monitored and evaluated.

Storage element 20 may contain additional files and data bases not shown in FIG. 2. For example, individual files which include background information on system users may be desirable. Other files and features (for example, to safeguard the confidentiality of certain information in storage element 20). may also be added.

Figure 3:
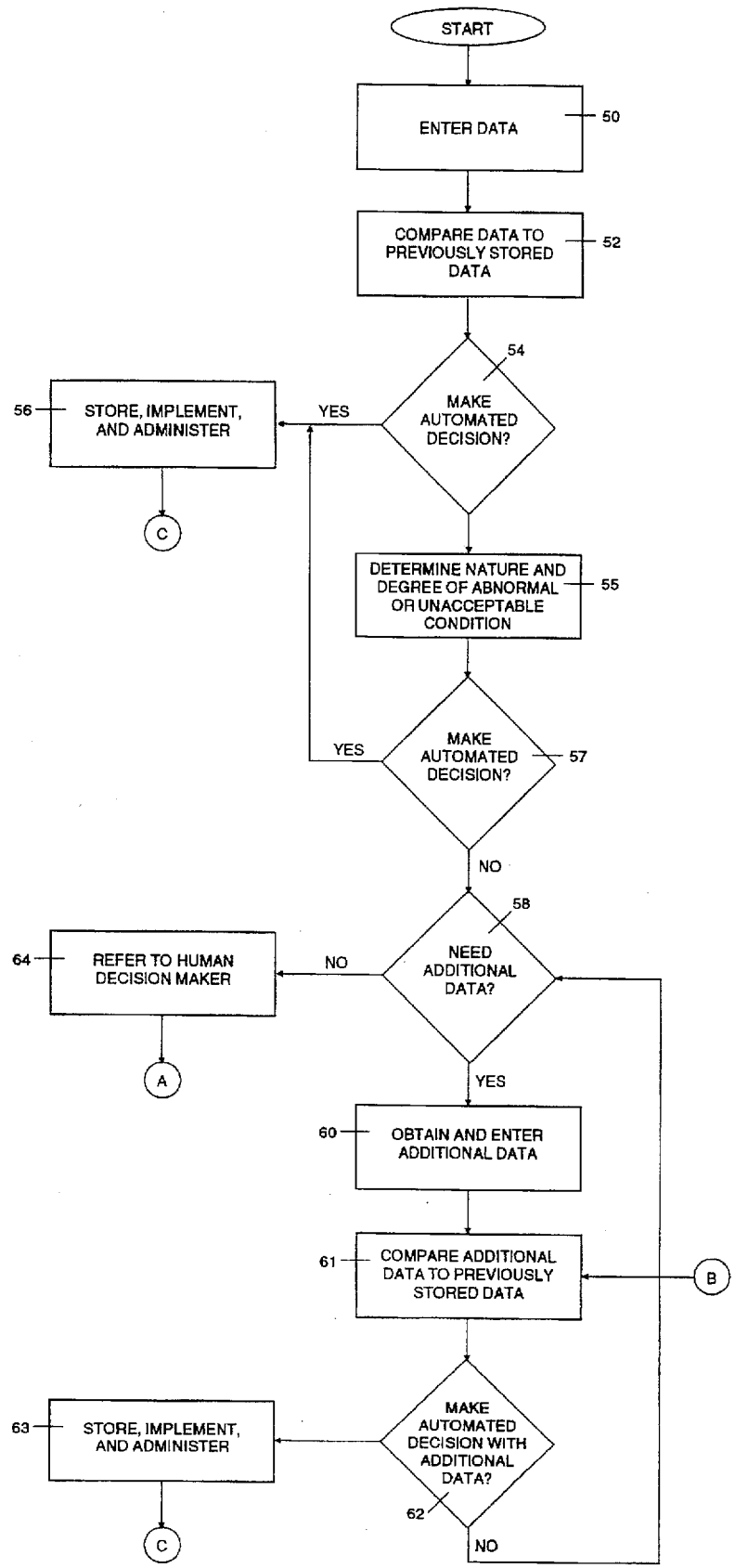
FIG. 3 shows a flow chart which illustrates features of the automated decision-making process of the present invention.
Figure 4:
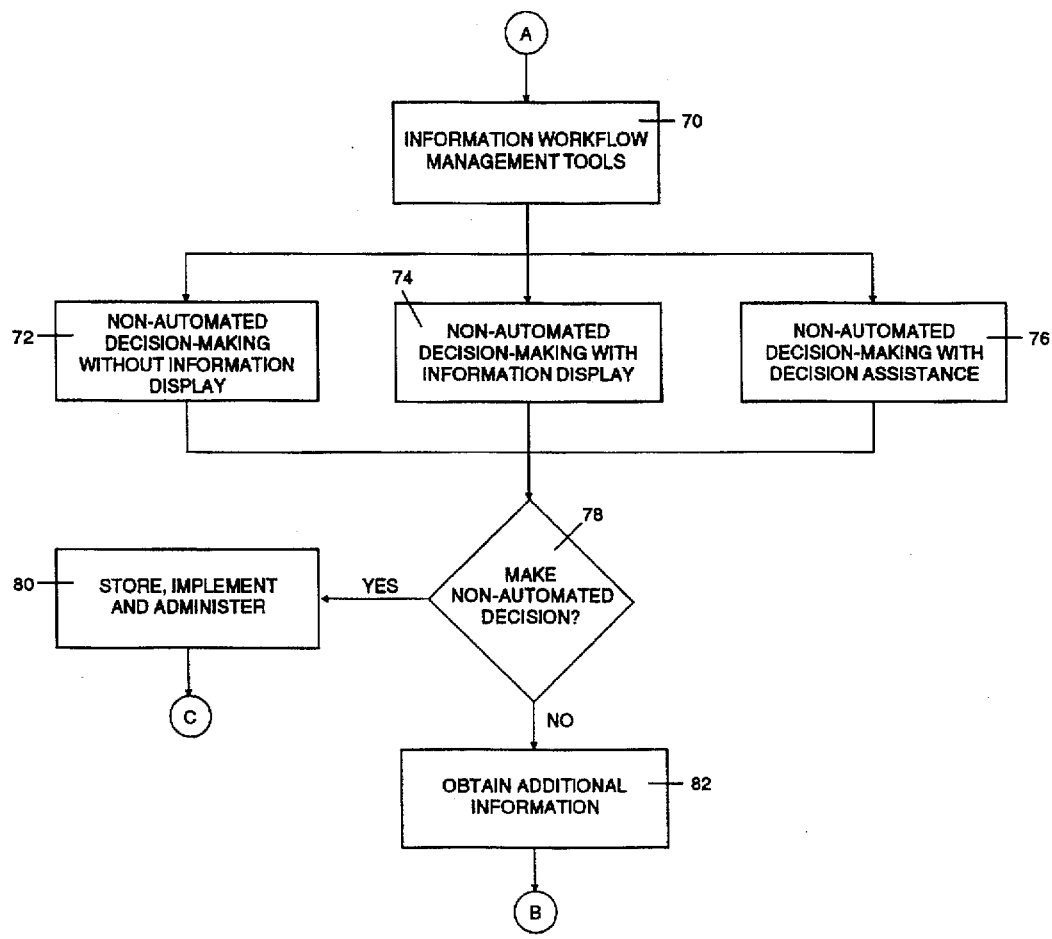
FIG. 4 shows a flow chart which illustrates information work flow management, information display and decision assistance features of the present invention.
Figure 5:
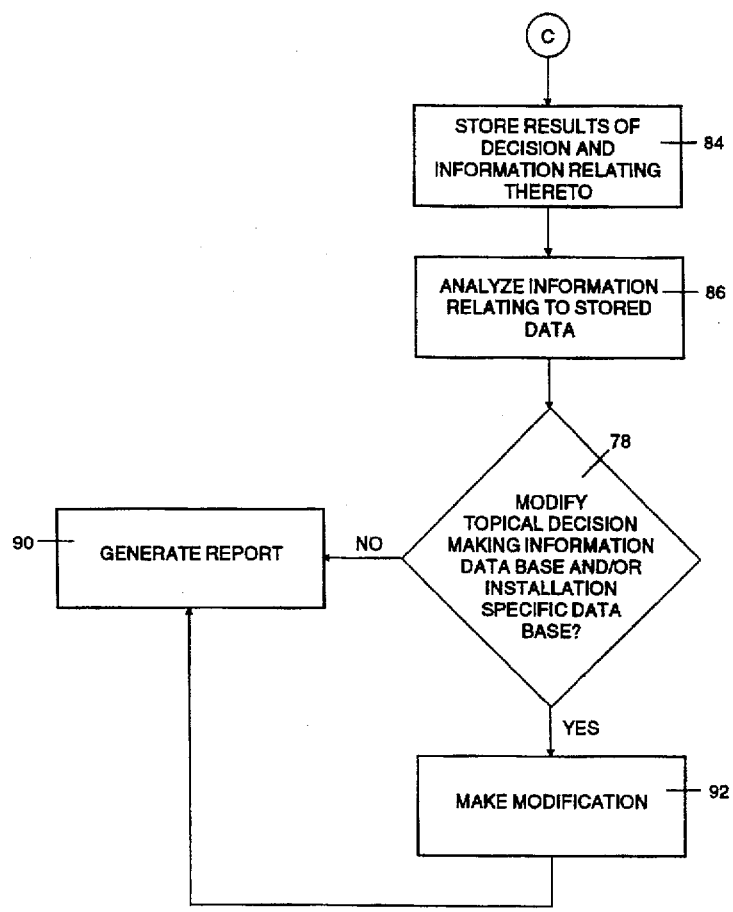
FIG. 5 shows a flow chart which illustrates the manner in which the instruction set or data relating to a specific topic of decision-making is modified in view of the results of previous decision-making activity.

FIGS. 3-5 show flow charts which illustrate the basic operation of the system of the present invention. Referring specifically to FIG. 3, block 50 represents an initial data entry step which allows for the entry of information pertaining to a specified decision-making process. The information entered into the system at this point is information gathered from a system user (or a client, patient, etc. of a system user) which will subsequently be compared to information which has been previously stored in the system. In the case of an investment decision, for instance, the information entered at this step might include user preferences for specific investment vehicles, user required or preferred rates of return, risk tolerance levels, and related information. In another application, for example the diagnosis of a medical condition, the information entered at this step may include a particular individual's medical history, pertinent symptoms, and other related information.

After initial data entry, a comparison or screening process is performed. This step is illustrated in the flow chart of FIG. 3 by block 52. The information to which the newly entered data is compared may, for example, be information contained in data base 22 of FIG. 2, installation specific data base 24 of FIG. 2, or information which may be classified as topical decision-making information and which is represented by block 26 of FIG. 2. The screening activity has to do with the recognition of abnormalities. The system compares the newly entered data to previously stored information and makes the decision of "normal versus abnormal" or "acceptable versus unacceptable." This entails having a model of what is perceived to be normal or acceptable within the system, and against which the newly entered data can be compared. If the newly entered data fits within the normal or acceptable limits of the model, a decision can be made, implemented and administered. This process is illustrated in FIG. 3 by blocks 54 and 56. For example, in processing a decision regarding the purchase of a stock, if a particular stock has an expected or calculated return which is greater than the return of a relatively risk-free investment, such as a treasury bond, and, for example, is performing at a rate which meets or exceeds the user's expectations or requirements, then it may be deemed to be performing acceptably and a decision to acquire or retain the stock can be made and implemented without further processing. Similarly, if information relating to the blood pressure of a patient falls within expected or acceptable limits, the system will identify this condition as being "normal" or "acceptable" and implement appropriate action. In the medical example, of course, a "normal" determination as to blood pressure may be but one of several pieces of information upon which an ultimate decision will be based.

If an initial decision cannot be made on the basis of the "screening" comparison to the stored model (i.e., if there is an abnormality or unacceptable condition), then the nature and degree of variance from the model is further defined. This step is illustrated by block 55 of FIG. 3. This process may entail viewing all of the information which is available in the system at that time and comparing that data with models of abnormality or unacceptable condition types to determine the nature of the abnormality. The models of abnormality or unacceptable condition types may, for example, be stored in block 36 of FIG. 2. Once the nature of the abnormality is determined, the degree of the problem may be determined by measuring the subject data against the normally acceptable limits. This measurement of problem degree goes beyond the "black and white" screening analysis described above, and allows the problem to be characterized in shades of gray. If the degree of the problem is not too great, then a decision can be made, implemented and administered, as described above and illustrated by block 57. If the degree of abnormality is too great, then the decision-making process must proceed. With reference to the investment decision referred to above, if the return on a stock is one-tenth of one percent below the return of a specified stock index, that performance may be deemed acceptable. However, if the return is one-tenth of one percent below the return available from a guaranteed security, such as a Treasury bill, the performance may be deemed unacceptable at this point.

If the nature and degree of the problem cannot be defined on the basis of the data additionally entered or previously stored in the system, then further information must be gathered to define the problem. This step is illustrated in FIG. 3 by block 58. For example, in the case of a decision-making process used in the context of a medical diagnosis, if a physician is unable to make a decision regarding a particular patient from that patient's medical history and symptoms, and the comparison of that information to models previously stored in the system, additional information, such as blood tests, X-rays, etc., may be required. Obtaining and entering this additional data is represented generally by block 60 in FIG. 3. When the additional information has been obtained, it is compared to the previously stored data (block 61) and the system again attempts to make an automated decision utilizing both the original and additionally received data (block 62). If a decision can be made at this time, the result is stored, implemented and/or administered (block 63). This process continues iteratively as each new piece of information is entered. The additional information is also compared to the previously available information for discrepancies. For example, a blood test or X-ray may produce information which is inconsistent with a patient's or doctor's subjectively determined symptoms or observations. If, at some point in this iterative process, it is determined that no additional data is needed and that an automated decision cannot be made, the matter is referred to a human decision-maker for resolution (block 64).

The nature and degree of problem is determined by comparing the data with a model stored in the topical decision-making information portion (26) of storage element 20. In a typical case, this process may involve the structural elements represented by the data stored in block 32, how those elements interrelate and function (block 34) and the types of problems (block 36) which may occur in the context of the user defined parameters and general decision-making steps.

For example, a person has a cough which is not normal, so the screening process defines this as abnormal. A cough is a manifestation of an abnormality of the respiratory system, so the system identifies data which corresponds to points of the respiratory system, such as the trachea or lungs, and data relating to how each works. Because more information is needed, the system requires an examination and a chest x-ray. If this additional information reveals that there is a fever and an infiltrate apparent from the chest x-ray, the system will search types of lung problems to determine which problems may cause or be related to these symptoms. Expert modules (block 40) may be utilized in this process. Based upon the information provided, the system may make an automated decision regarding a course of treatment. It may, for example, determine that the antibiotic Penicillin is necessary to combat the conditions causing the fever. On the other hand, if the patient's medical history shows that this patient has exhibited allergic reactions to Penicillin in the past, some other course of action would be prescribed. If some other condition, for example cancer, had been diagnosed, then the different forms of treatment for cancers (e.g., surgery, radiation or chemotherapy) would be evaluated by the system and recommended as appropriate.

FIG. 4 shows a flow chart which represents a portion of the subject system designed to help a human decision maker make decisions which cannot be made automatically by the process illustrated in FIG. 3. Block 70 represents information work flow management tools available to the human decision-maker utilizing the system. Such tools may include:

(a) an in-tray of cases or material to be used in the decision-making process. This in-tray will display the cases or materials for the decision-maker, and allow the decision maker to select a case upon which to proceed;

(b) problem page processing tools which include a mechanism to display the problems or non-correspondences which the system has identified, as well as recommendations from the system relating to resolution of the problem or the need for additional data or information relating to the decision;

(c) historical data relating to the decision;

(d) a status function for identifying the status of cases under review;

(e) a note pad function;

(f) an internal referral function for obtaining second opinions from other decision-makers; and (g) telecommunication tools, such as electronic mail connections, a letter generator, and similar tools used for notifying others of decisions, the need for additional information, etc.

When a case is selected from the in-tray provided in the work flow management tools, the system user can proceed along any of three alternative routes. These three alternatives are generally represented in FIG. 4 by blocks 72, 74, and 76. Blocks 72 and 74 allow for non-automated decision-making, with or without the aid of information displayed from the system data bases. Block 76 illustrates the option for making a non-automated decision with decision assistance from the system. Such assistance may take the form of providing the user with access to the expert system modules utilized by the system in the automated decision-making process. Based on the information available to the system and the structure of the expert system modules, the system may make recommendations to the human decision maker, which recommendations the decision maker can accept or ignore. In the medical diagnosis application, for example, the system may recommend to a physician that Penicillin be considered in the treatment of a particular condition. However, based upon other considerations (e.g., the possibility of an allergic reaction), the physician may opt for an alternative course of therapy. After concluding one or more of the operations represented by blocks 72, 74 and 76, the decision maker may make a non-automated decision, as represented by block 78. If such a decision is made, the result is stored, implemented and administered in operations which are generally represented by block 80. If a decision is not made, additional information is obtained (block 82) and the case is returned to the automated portion of the system (block 61) for further iterative processing.

FIG. 5 illustrates an important aspect of a preferred embodiment of the present invention. Each time a decision is made (e.g., blocks 56, 63 and 80), the results of the decision, and information relating thereto, are stored (block 84) in a portion of storage element 20. These results and information are then analyzed and compared (block 86) to information subsequently received relating to the actual outcome of the subject matter of the decision-making. Based upon this analysis, elements of information stored in the storage element (for example, elements of information in the topical decision-making information data base or the installation specific data base) are added, deleted, or modified (blocks 88 and 92) based on the comparison and analysis of the subsequently received data. Whether or not a modification is made, a report can be generated (block 90) at this stage for use in evaluating the performance of the system.

Although the subject invention has been described in terms of a single system having a single storage element containing information specific to a particular topic of decision-making (i.e., investments or medical diagnosis), a "single" system may, in fact, contain many such storage elements relating to a corresponding number of decision-making topics. Alternatively, a single storage element or device may be subdivided into a plurality of areas, each specific to a particular topic of decision-making. As previously stated, the invention is not intended to be limited to a particular type of information storage or data processing hardware. In this regard, some types of storage elements may intermingle information relating to different topics of decision-making within the same geographical or structural storage areas without departing from the spirit of the present invention.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. An automated system for use in decision-making processes, comprising information processing means and storage means, input and output means for receiving and communicating data and processed information to and from said processing means and storage means, said storage means comprising a plurality of components, each component containing selected elements of declarative background knowledge specific to a selected decision-making process screening means for comparing selected elements of data received from the input means to defined elements of the background knowledge stored in the storage means and for implementing a first decision operation if the inputted data corresponds to respective elements of the background knowledge, decision-making means for identifying inputted data which does not correspond to respective elements of the background knowledge, means for determining the nature and degree of said non-correspondence, and means for comparing additional elements of data received from the input means, reflective of the nature and degree of said non-correspondence, to additional elements of the background knowledge and for implementing a second decision operation based on said comparison.

2. An automated system according to claim 1, wherein said means for determining the nature of said non-correspondence comprises means for reviewing the non-corresponding data and comparing that data to previously stored data to determine the nature of said non-correspondence.

3. An automated system according to claim 2, wherein the non-corresponding data is compared to data representative of at least one of a plurality of previously stored model data sets to determine the nature of non-correspondence existing between the inputted data and the background knowledge.

4. An automated system according to claim 2, wherein said means for determining the degree of non-correspondence comprises means for reviewing the non-corresponding data and comparing that data to previously stored data to determine the degree of said non-correspondence.

5. An automated system according to claim 4, wherein the non-corresponding data is compared to a previously stored range of data values to determine the degree of non-correspondence existing between the data and the background knowledge.

6. An automated system according to claim 1, wherein said decision-making component further comprises means for identifying elements of the inputted data which do not correspond to respective elements of the background knowledge and for which the nature and degree of non-correspondence cannot be determined.

7. An automated system according to claim 6, wherein said means for implementing at least one of the first and second decision operations comprises means for identifying a plurality of alternative options, each of which are alternatively selected to form at least a part of said decision operation, means for comparing expected outcomes of said options, and means for selecting from among said options.

8. An automated system according to claim 7, further comprising means for storing data relating to the decision operations implemented, means for comparing said data to subsequently received data relating to an outcome of the decision-making process, and means for adding to, deleting from or modifying at least one of the components of the storage means based on said comparison.

9. An automated system according to claim 6, further comprising means for requesting additional data pertaining to the selected decision-making process, means for comparing the additional data to additional elements of the background knowledge, and means for implementing one of said first and second decision operations.

10. An automated system according to claim 9, further comprising means for comparing the additional data to the previously inputted data, and for identifying discrepancies existing between corresponding elements of said data.

11. An automated system according to claim 1, wherein said means for implementing at least one of the first and second decision operations comprises means for identifying a plurality of alternative options, each of which are alternatively selected to form at least a part of said decision operation, means for comparing expected outcomes of said options, and means for selecting from among said options.

12. An automated system according to claim 1, further comprising means for storing data relating to the decision operations implemented, means for comparing said data to subsequently received data relating to an outcome of the decision-making process, and means for adding to, deleting from or modifying at least one of the components of the storage means based on said comparison.

13. An automated system according to claim 1, further comprising means for selectively compiling data relating to the decision operations implemented for purposes of evaluating the quality and consistency of decisions made.

14. An automated method for use in decision-making processes using a system having information processing means and storage means, input and output means for receiving and communicating data and processed information to and from said processing means and storage means, said storage means comprising a plurality of components, each component containing selected elements of declarative background knowledge specific to a selected decision-making process, said automated method comprising the steps of:

(a) inputting data pertaining to the selected decision-making process;

(b) comparing selected elements of the inputted data to defined elements of the background knowledge stored in the storage means and implementing a first decision operation if the inputted data corresponds to respective elements of the background knowledge;

(c) identifying elements of the inputted data which do not correspond to respective elements of the background knowledge;

(d) determining the nature and degree of said non-correspondence; and (e) comparing additional elements of data received from the input means, based upon the nature and degree of said non-correspondence, to elements of the background knowledge and implementing a second decision operation based upon said comparison.

15. The method of claim 14, further comprising the step of reviewing the non-corresponding data and comparing that data to previously stored data to determine the nature of said non-correspondence.

16. The method of claim 15, wherein the non-correspondence data is compared to data representative of at least one of a plurality of previously stored model data sets to determine the nature of non-correspondence existing between the inputted data and the background knowledge.

17. The method of claim 15, further comprising the step of reviewing the non-corresponding data and comparing said non-corresponding data to previously stored data to determine the degree of said non-correspondence.

18. The method of claim 17, wherein the non-corresponding data is compared to a previously stored range of data values to determine the degree of non-correspondence existing between the inputted data and the background knowledge.

19. The method of claim 14, further comprising the step of identifying elements of the inputted data which do not correspond to respective elements of the background knowledge and for which the nature and degree of non-correspondence cannot be determined.

20. The method of claim 19, further comprising the additional steps of identifying a plurality of alternative options, each of which are alternatively selected to form at least a part of said decision operation, comparing expected outcomes of said options, and selecting from among said options.

21. The method of claim 19, further comprising the steps of storing data relating to the decision operations implemented, comparing said data to subsequently inputted data relating to an outcome of the decision-making process, and adding, deleting, or modifying the background knowledge in at least one of the components based on said comparison.

22. The method of claim 19, further comprising the steps of requesting additional data pertaining to the selected decision-making process, inputting and comparing the additional data to additional elements of the background knowledge, and implementing one of said first and second decision operations.

23. The method of claim 22, further comprising the additional step of comparing the additional data to the previously inputted data, and identifying discrepancies existing between corresponding elements of said data.

24. The method of claim 14, comprising the additional steps of identifying a plurality of alternative options, each of which are alternatively selected to form at least a part of said decision operation, comparing expected outcomes of said options, and selecting from among said options.

25. The method of claim 14, further comprising the additional steps of storing data relating to the decision operations implemented, comparing said data to subsequently received data relating to an outcome of the decision-making process, and adding, deleting or modifying the background knowledge in at least one of the components based on said comparison.

26. The method of claim 14, further comprising the additional step of selectively compiling data relating to the decision operations implemented for purposes of evaluating the quality and consistency of decisions made.

27. An automated system according to claim 1, wherein said components of the storage means comprise two or more of a group which includes a data base, an installation specific data base, topical decision-making information, a decision-making file, and a management information data base.

28. An automated system according to claim 27, wherein said data base contains general background knowledge relevant to the selected decision-making process.

29. An automated system according to claim 27, wherein said installation specific data base contains rules, guidelines, procedures and related information specific to a particular system user.

30. An automated system according to claim 27, wherein said topical decision-making information comprises at least one of structural elements, functional elements, problem elements and decision-making reference material relating to the selected decision-making process.

31. An automated system according to claim 30, wherein said structural elements include major components of declarative background knowledge used in the selected decision-making process.

32. An automated system according to claim 30, wherein said functional elements comprise elements of knowledge which relate to how the structure elements function.

33. An automated system according to claim 30, wherein said problem elements include statements or definitions of problems which may occur with the structural elements or the functional elements.

34. An automated system according to claim 30, wherein said decision-making reference material includes at least one of a library of abbreviations and a dictionary of terms.

35. An automated system according to claim 30, wherein at least one of said structural, functional and problem elements includes a programmed knowledge base having one or more expert modules relating to the selected decision-making process.

36. An automated system according to claim 27, wherein said decision-making file includes at least one of criteria, alternatives, weighing functions, and utilities for use in the selected decision-making process.

37. An automated system according to claim 27, wherein said management information data base comprises results of selected decisions made by the system and each user of the system.

* * * * *